United States Patent
Farley et al.

[11] Patent Number: 5,902,233
[45] Date of Patent: May 11, 1999

[54] ANGLING SURGICAL RETRACTOR APPARATUS AND METHOD OF RETRACTING ANATOMY

[75] Inventors: Daniel K. Farley, Traverse City; Anthony J. Mulac, East Jordan, both of Mich.

[73] Assignee: Thompson Surgical Instruments, Inc., Traverse City, Mich.

[21] Appl. No.: 08/763,711

[22] Filed: Dec. 13, 1996

[51] Int. Cl.$^6$ .................................................. A61B 17/00
[52] U.S. Cl. ........................ 600/213; 600/215; 600/227
[58] Field of Search ................................ 600/201, 213, 600/215, 227, 228, 229, 231, 232, 233

[56] References Cited

U.S. PATENT DOCUMENTS

| | | | |
|---|---|---|---|
| 2,623,517 | 12/1952 | Barlow et al. | 600/233 |
| 3,196,865 | 7/1965 | Rose | 600/234 X |
| 3,221,743 | 12/1965 | Thompson et al. | |
| 3,965,890 | 6/1976 | Gauthier | |
| 4,421,108 | 12/1983 | Cabrera | |
| 4,617,916 | 10/1986 | LeVahn et al. | |
| 4,718,151 | 1/1988 | LeVahn et al. | |
| 4,949,707 | 8/1990 | LeVahn et al. | |
| 4,971,038 | 11/1990 | Farley | |
| 5,020,195 | 6/1991 | LeVahn | |
| 5,025,780 | 6/1991 | Farley | |
| 5,242,240 | 9/1993 | Gorham | |
| 5,375,481 | 12/1994 | Cabrera et al. | 600/233 X |

FOREIGN PATENT DOCUMENTS

| | | | |
|---|---|---|---|
| 1246994 | 7/1986 | U.S.S.R. | 600/233 |
| 1333317 | 8/1987 | U.S.S.R. | 600/215 |

*Primary Examiner*—Jeffrey A. Smith
*Attorney, Agent, or Firm*—McAndrews, Held & Malloy, Ltd.

[57] ABSTRACT

A physical retractor apparatus and method for retracting anatomy during surgery wherein the apparatus includes a handle rod, a body portion, a retractor blade and a mechanism which allows the retractor blade to be angularly adjusted, and secured, to one of any number of angular positions. The handle rod may be attached to an extension arm of a surgery support frame via a standard joint clamp. Once secured, the retractor blade may be manually positioned to the desired angular position and secured in place. The adjustment mechanism includes a notched push bar which engages a brace member of the retractor blade thereby effecting movement of the retractor blade when the push bar is moved by the user. A releasable engagement member then engages one of several notches in the push rod to inhibit any further movement of the retractor blade. Pursuant to the preferred embodiment of the present invention, the retractor blade may be precisely adjusted to its desired angular position with respect to the retracted anatomy without having to also adjust the position of the handle rod itself.

19 Claims, 7 Drawing Sheets

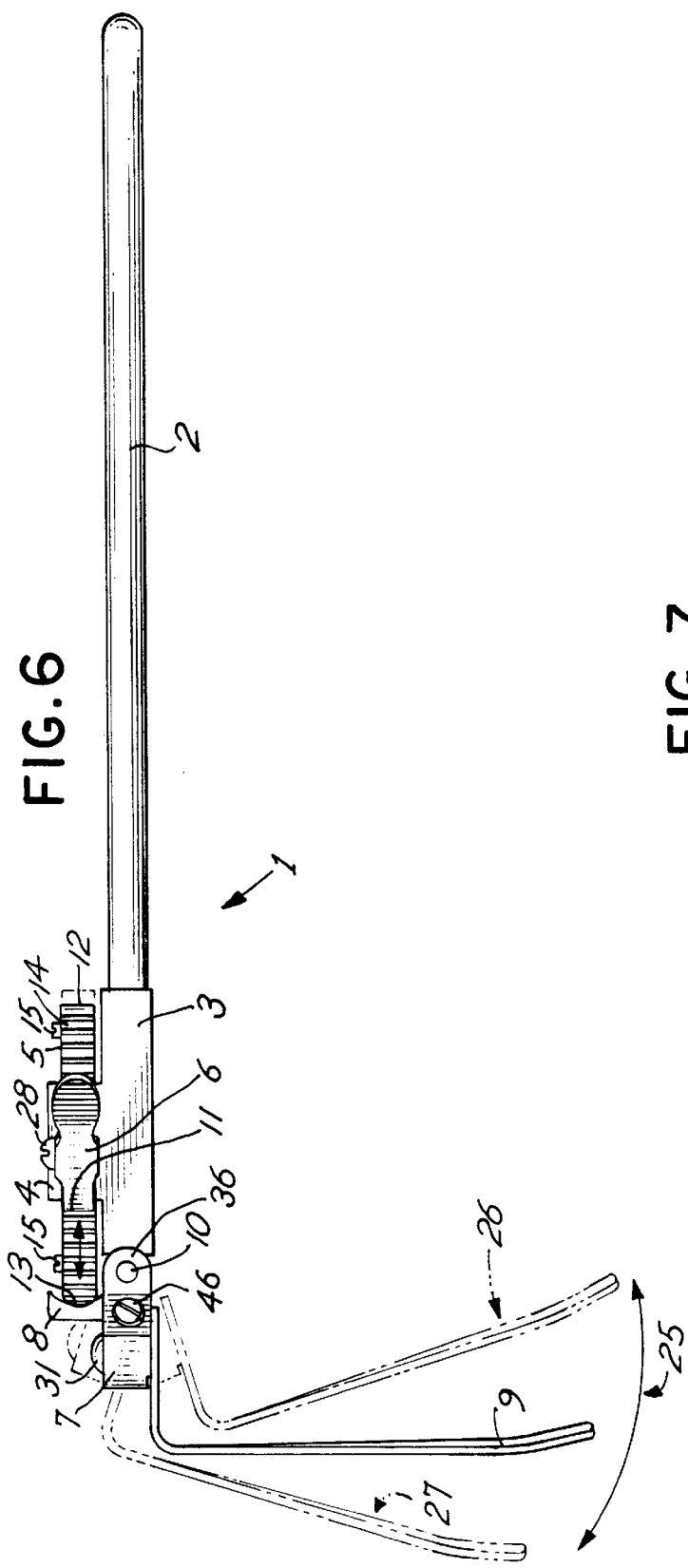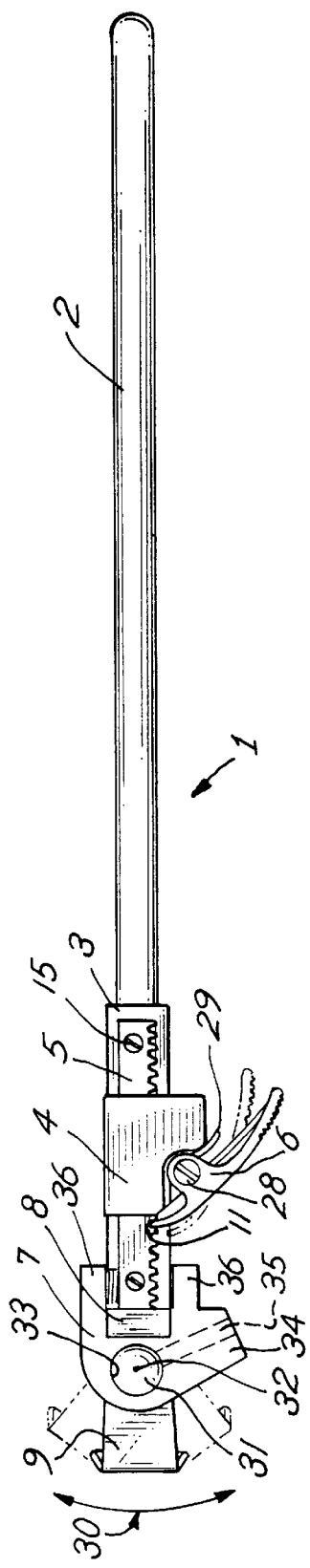

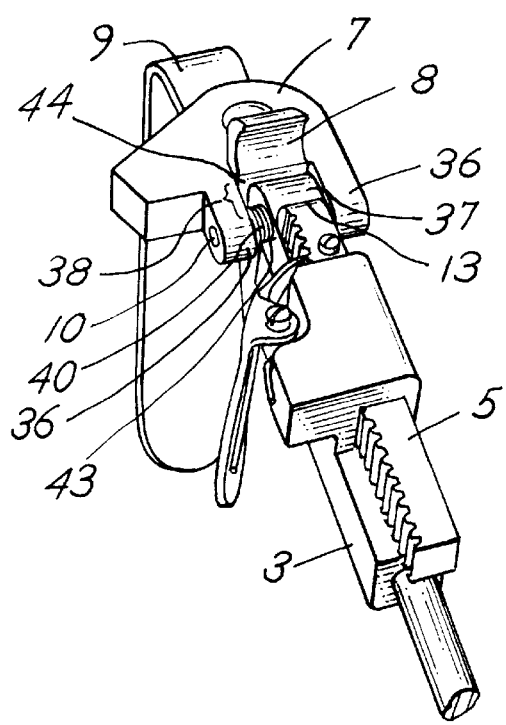
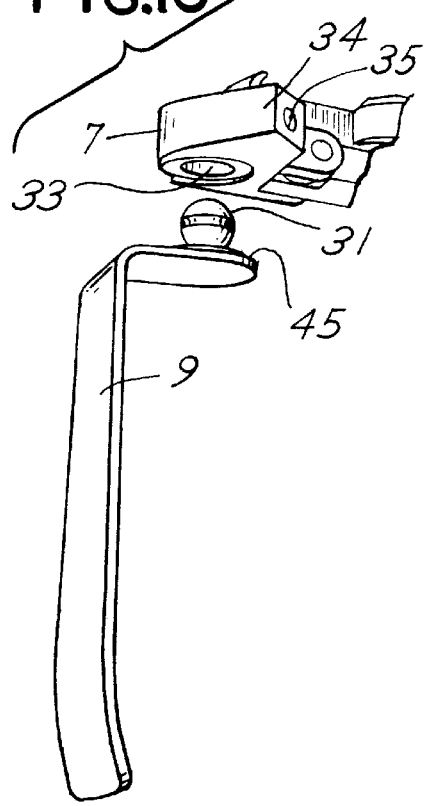
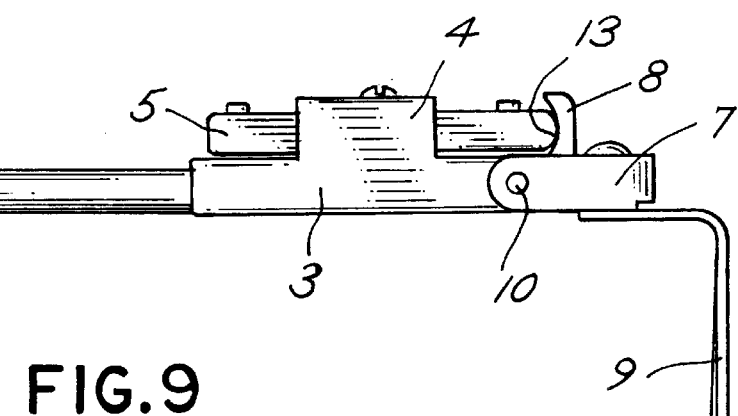

ANGLING SURGICAL RETRACTOR APPARATUS AND METHOD OF RETRACTING ANATOMY

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

The present invention relates to a surgical apparatus for retracting anatomy to provide exposure of the operative site and, more particularly, to a retraction apparatus in which the retractor blade is angularly-adjustable.

In surgical operations, it is customary to use a retraction device in order to properly access internal organs and bone structures. Such devices are particularly designed to hold back the anatomy in the immediate area of the operative site to enable a surgeon to have both an optimal view of the site and a sufficiently-open area within which to work.

Known retraction systems typically include a frame assembly mounted to an operating table, a plurality of support rods extending from such frame, a retractor device having a blade and handle, and a variety of clamping devices for use in securing the support rods to the frame and the retractor devices to the support rods. The majority of the above-described retractor system is located above the operative site where surgery is to be performed—the retractor blade itself being the only component in substantial contact with the retracted anatomy.

The usefulness of any retractor device is necessarily limited by the number of ways that the retractor can be positioned with respect to the retracted anatomy as well as the ease with which the surgeon can adjust the relative position of the retractor both before and during surgery. Obviously, the less obstructive and more versatile a retractor device is, the more desirable it becomes for use in the above-described manner.

Given the variances in patient size as well as the types of surgery with which retractor systems are used, a variety of adjustment mechanisms have been developed in this field of art. One such area which has seen improvements is that relating to the configuration of support structures. Through various combinations of support rod inter-connectivity, these developments assisted in allowing a retractor (blade and handle) to be more particularly positioned at the operative site. The following patents are illustrative of such developments: U.S. Pat. Nos. 4,617,916, 4,717,151, 4,949,707 and 4,971,038.

Improvements also have been observed with regard to the clamping devices used to inter-connect support rods and retractor handles. By increasing the pivotability of such elements, the precision and ease with which retractors (again, both blade and handle) can be positioned has increased. Illustrative of such developments include the following: U.S. Pat. Nos. 4,421,108, 5,020,195, 5,025,780 and 5,242,240.

Additional developments in this field of art include the use of interchangeable retractor blades with a single retractor handle assembly. Such interchangeable blades come in a variety of angles whereby the desired angle of retraction may be obtained by first attaching the proper retractor blade to the handle and then securing the entire assembly to a support rod. In addition, it is now known that such detachable retractor blades can "swivel" in place to compensate for inexact positioning of a blade handle or support rod and ensure that the face of the retractor blade remains flush with the retracted anatomy.

In light of the above-described developments, however, there is nothing in the prior art which provides for the acute angular adjustment of the retractor blade itself so as to precisely position the blade without adjusting the blade handle, clamping member or associated support rod. Indeed, with all of the retractor systems known in the prior art today, the ultimate positioning of a retractor blade requires, at a minimum, that such blade and corresponding handle assembly be adjusted via a clamping member at the associated support rod.

It is therefore an object of the present invention to provide a surgical retractor apparatus having a retractor blade which is angularly adjustable with respect to its handle.

It is a second object of the present invention to provide an angling surgical retractor apparatus whereby the angular position of the retractor blade may be adjusted after the handle of the apparatus is secured to a support rod.

It is another object of the present invention to provide an angling surgical retractor apparatus whereby the retractor blade may be easily secured in its desired angular position.

It is a further object of the present invention to provide an angling surgical retractor apparatus whereby the retractor blade may swivel in place.

In addition, it is an object of the present invention to provide an angling surgical retractor apparatus whereby a variety of retractor blades may be interchangeably used with the apparatus.

Lastly, it is an object of the present invention to provide an angling surgical retractor apparatus having a compact angling mechanism to ensure an unobstructed view for the surgeon.

BRIEF SUMMARY OF THE INVENTION

These and other objects of the present invention are achieved in a surgical retraction apparatus which retracts anatomy during all types of surgery. The apparatus is particularly applicable to those delicate procedures wherein it is desirable to have maximum exposure deep in the wound through a micro-incision. The device includes a handle rod which is intended to be fastened to a frame structure of a surgical operating table via some form of clamping device. At an end of the handle rod opposite that which is clamped, the device includes a pivoting head member to which one of any number of interchangeable retractor blades is connected. Mounted on the top of the handle rod is a slidable push rod which positions the head member and associated retractor blade in one of any number of angular positions. Once the push rod and retractor are in the desired position, the thumb switch engages the push rod to inhibit any further movement.

In accordance with the preferred embodiment of the present invention, the handle rod may be secured to a support rod or rail member using a standard clamping device whereby the retractor blade, generally, is in contacting position with the anatomy to be retracted. Thereafter, and without any further adjustments being made to the handle rod itself or other supporting members, the retractor blade may be particularly angled either inwardly or outwardly so as to retract the anatomy exactly as the surgeon desires.

BRIEF DESCRIPTION OF THE SEVERAL VIEWS OF THE DRAWING

FIG. 6 is a left side view of the angling surgical retractor apparatus.

FIG. 7 is a top view of the angling surgical retractor apparatus.

FIG. 8 is a top view of the pivoting mechanism and associated components of the angling surgical retractor apparatus.

FIG. 9 is a right side view of the angling surgical retractor apparatus.

FIG. 10 is an underside perspective view of the angling surgical retractor apparatus with retractor blade detached.

DETAILED DESCRIPTION OF THE INVENTION

Figure 1:
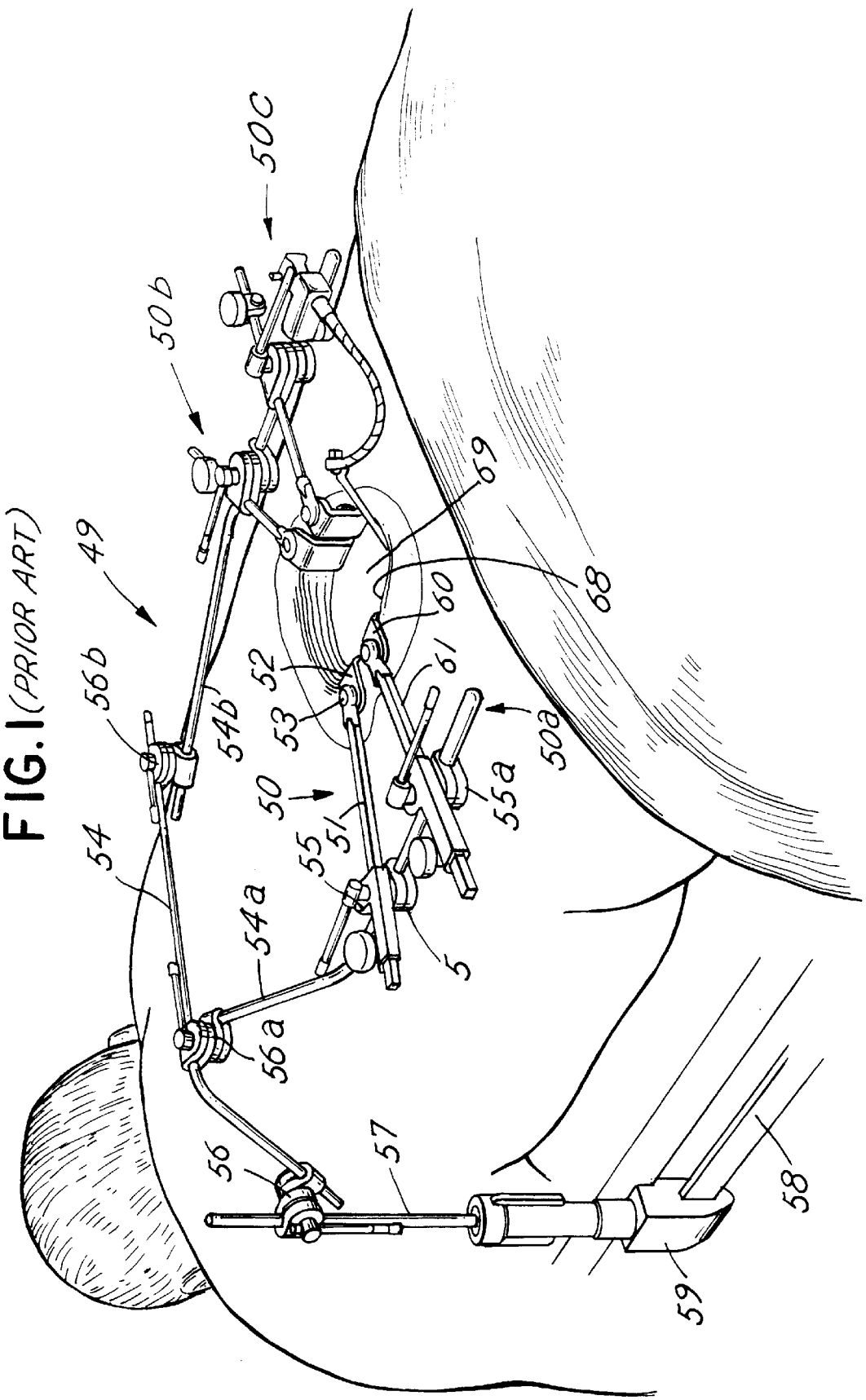
FIG. 1 is a perspective view of a surgical retraction system of the prior art.

Referring to FIG. 1, a typical surgical retraction system 49 known in the prior art includes an adjustable rail clamp 59 which is securable to a horizontal rail 58 of a conventional operating table (not shown). A support post 57 extends vertically upward from rail clamp 59 providing a support for extension arm 54. Extension arm 54 is secured to support post 57 with a multi-directional joint clamp 56. Additional joint clamps 56(a) and 56(b) are disposed along extension arm 54 for rigidly securing additional extension arms 54(a) and 54(b).

At a further point along extension arm 54(a), a standard retractor device 50 is secured in place. Specifically, mounting rod 51 is affixed to extension arm 54(a) via joint clamp 5 once retractor blade 52 is set in the desired position within operative site 69.

Each such retractor device 50 includes a retractor blade 52, mounting rod 51 and (usually) a swivel member 53. Retractor blade 52 extends downwardly into the operative site 69 and retracts anatomy 68 so as to make such operative site 69 accessible to the surgeon. Swivel member 53 allows retractor blade 52 to swivel in place thus allowing retractor blade 52 to maintain flush contact with anatomy 68 at all times.

The overall surgical retraction system 49 can be adapted to provide additional retraction by simply adding components such as an addition extension arm 54(b) and additional retractor devices such as 50(a), 50(b) and 50(c).

Should it be decided that the angle with which retractor blade 52 engages anatomy 68 must be changed, one is basically faced with two alternatives. First, retractor blade 52 may be replaced with a different retractor blade having the desired angular shape. Alternatively, one may raise or lower extension arm 54(a) so as to correspondingly change the angular position of retractor blade 52. This second option, however, necessarily requires that one also adjust the angular position of retractor 60 since mounting rod 61 of retractor 60 is also secured to extension arm 54(a) via joint clamp 55(a).

Figure 2A:
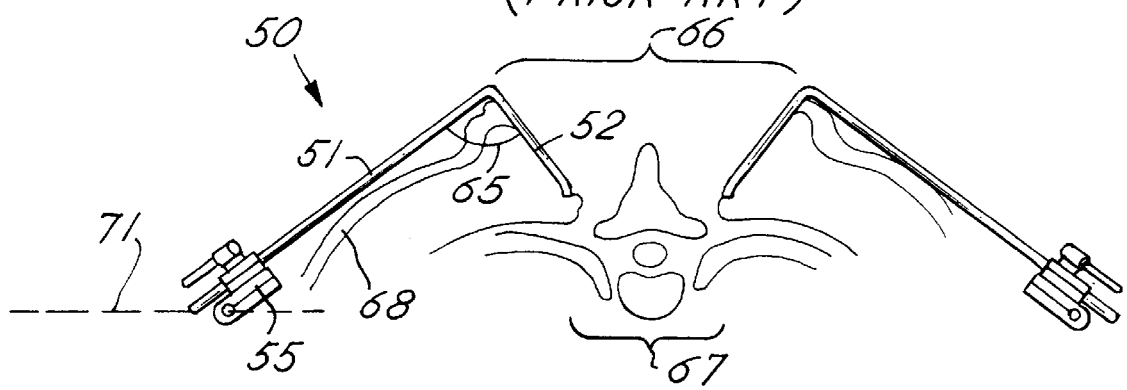
FIGS. 2(a), 2(b) and 2(c) are side views of prior art retractor devices as used in three different angular positions.
Figure 2B:
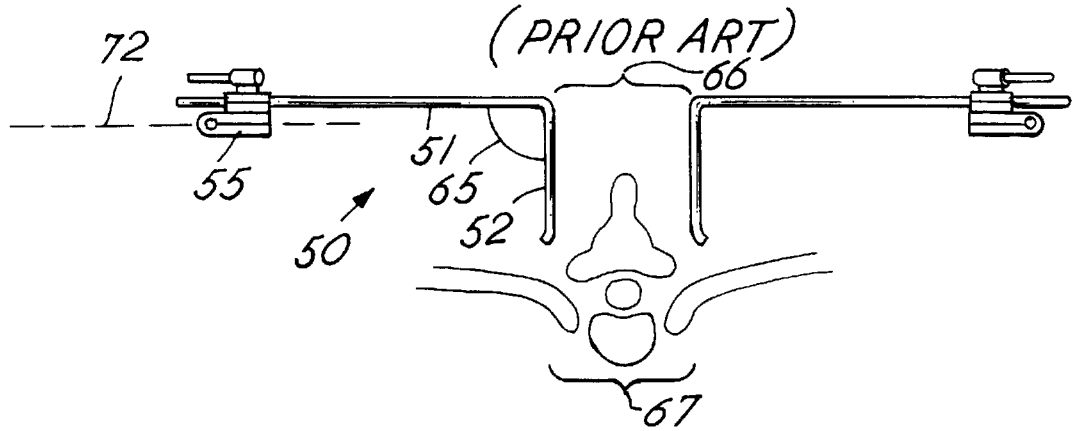
Figure 2C:
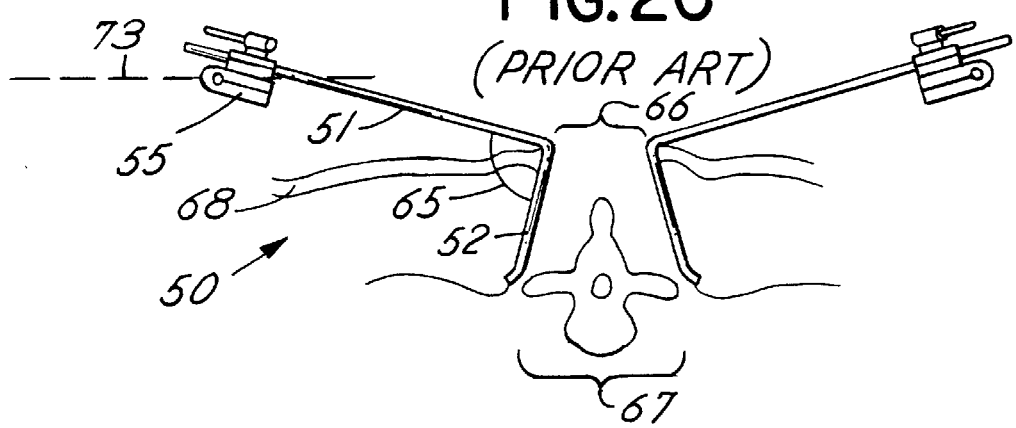

Indeed, as shown in FIGS. 2(a), 2(b) and 2(c), changing the angle at which retractor blade 52 engages anatomy 68 correspondingly requires that the mounting rod 51 of the retractor apparatus 50 be repositioned as well. For example, FIG. 2(a) shows a typical retractor apparatus 50 which is positioned in connection with the operative site so as to maximize the surgical opening 66 while minimizing the lower operating area 67. Such configuration requires that the joint clamp 55 which secures the retractor device 50 in this position be connected to an extension arm (not shown) at a general horizontal mounting level 71.

Should the surgeon decide, however, that an adjustment should be made whereby the surgical opening 66 would be made substantially equal to the lower operating area 67, the retractor device 50 must be adjusted as shown in FIG. 2(b). Given that this retractor device 50 maintains a substantially 90° angle 65 between its mounting rod 51 and retractor blade 52 at all times, the mounting rod 51 and joint clamp 55 must be repositioned and secured at a different horizontal mounting level 72.

FIG. 2(c) offers a further example of the primary drawback of retractor devices 50 of the prior art whereby maximum exposure of the lower operating area 67 is desired through a minimal surgical opening 66. In this case, mounting rod 51 and corresponding joint clamp 55 are repositioned at an even higher horizontal mounting level 73.

Figure 3:
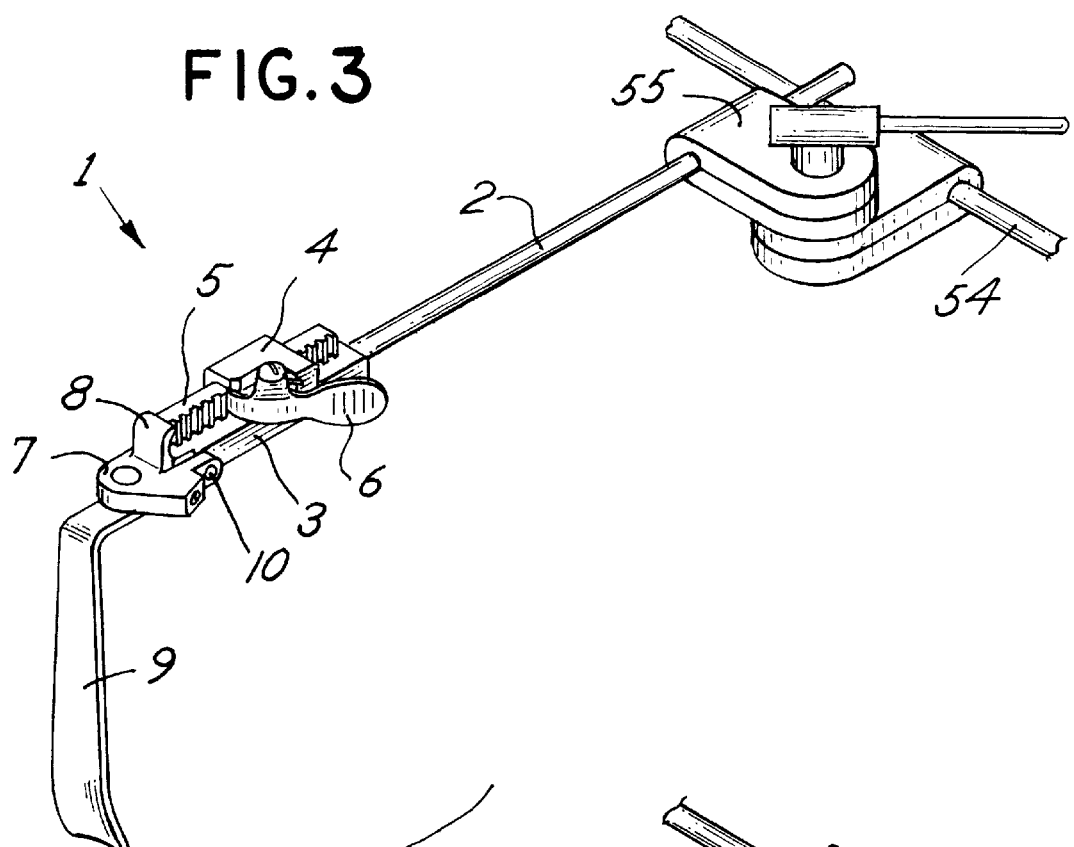
FIG. 3 is a perspective view of the preferred embodiment of the angling physical retractor apparatus.

Turning now to FIG. 3, the angling surgical retractor apparatus 1 is shown mounted to a standard extension arm 54 via a multi-directional joint clamp 55. The primary components of the preferred embodiment include a handle rod having a cylindrical mounting arm 2 and a body segment 3, a push rod housing 4, a push rod 5, a thumb switch 6, and a retractor blade member formed of a blade 9 and a head member 7. As can be observed, the general shape of the overall retractor apparatus 1 is substantially similar to that which is already known in the prior art. However, blade 9 and associated head member 7 are angularly adjustable about axle 10 with respect to body segment 3.

Figure 4A:
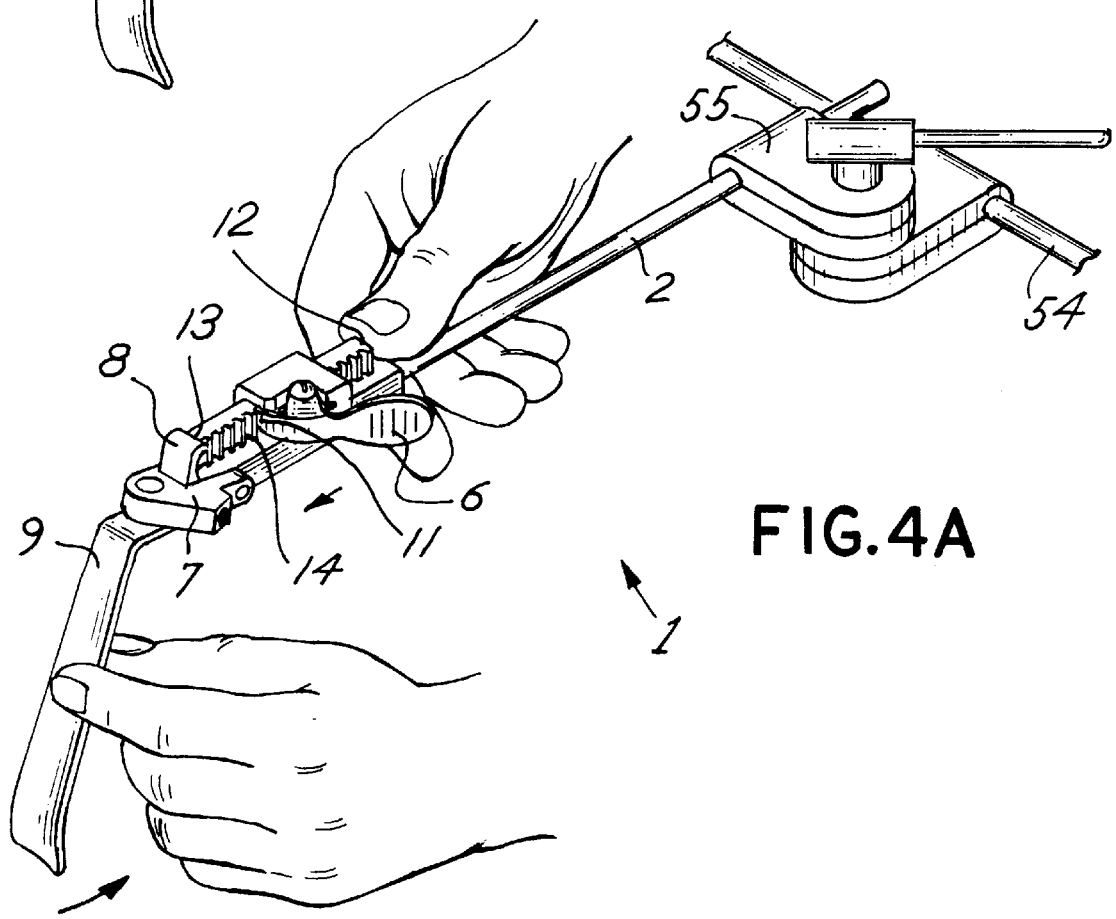
FIGS. 4(a) and 4(b) are perspective views of the angling surgical retractor apparatus being manually adjusted to provide for an acute angle of retraction between the handle and retractor blade 4(a) and an obtuse angle of retraction 4(b).

As shown in FIG. 4(a), a user may angle blade 9 inwardly with respect to body segment 3 by simply moving the blade 9 inwardly while simultaneously pushing the rearward end 12 of push rod 5 forwardly with the other hand. It should be noted that a spring member 40 (shown in FIG. 8) serves to keep the brace 8 of head member 7 in contacting relation with a forward end 13 of push rod 5 when the device is in a stationary position.

Once blade 9 is in its desired position, a leading edge 11 of thumb switch 6 engages one of a plurality of notches 14 which are formed in one side of push rod 5 so as to secure the apparatus in the desired position. Thumb switch 6 is rotatably secured to push rod housing 4 via screw 28 and is biased by spring member 29 (shown in FIG. 7) so as to keep leading edge 11 in contacting relation with a notch 14 of push rod 5. When not engaged by either thumb switch 6 or brace 8, push rod 5 is free to slidably move within push rod housing 4.

Figure 4B:
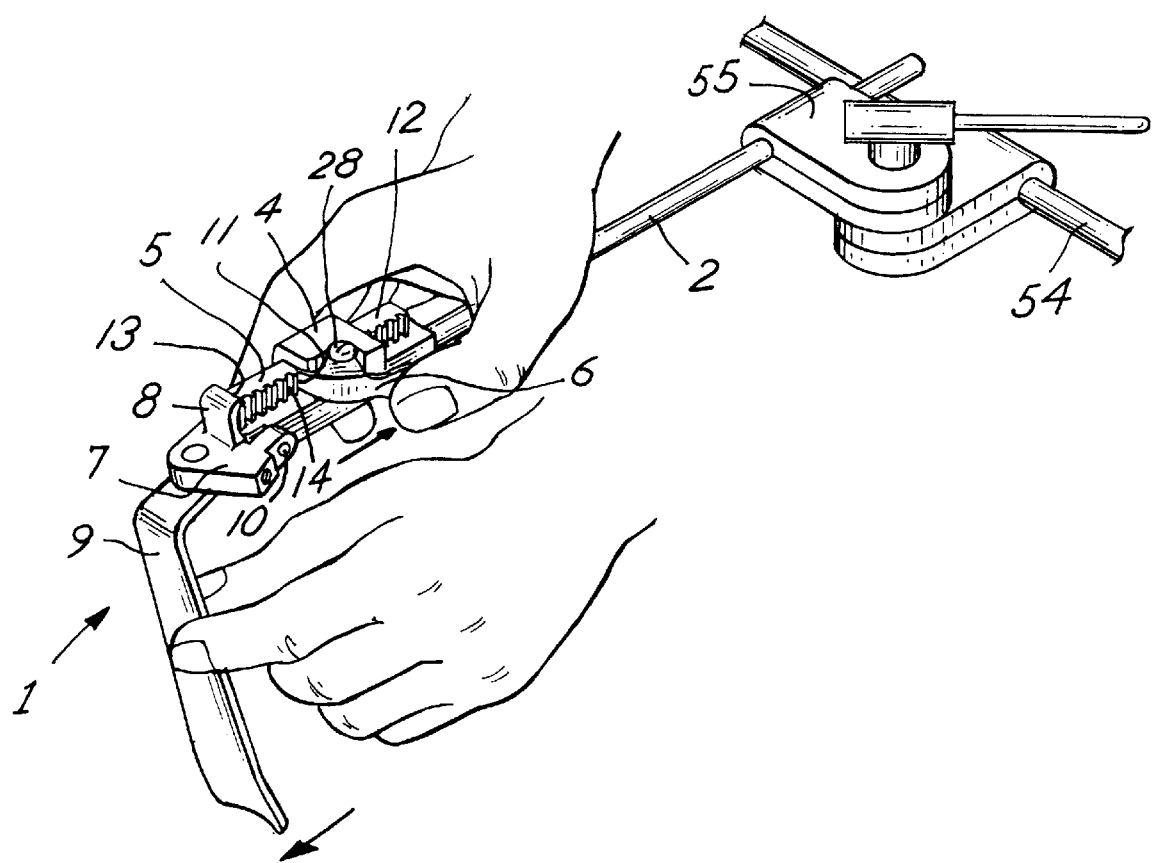

To adjust the blade 9 to a less-acute angle as shown in FIG. 4(b), the operator of the angling surgical retractor apparatus 1 uses one hand to press down upon thumb switch 6 to disengage leading edge 11 from a notch 14 of the push rod 5 and then uses the other hand to reposition the blade 9 to the desired angle. Once the blade 9 is repositioned, thumb switch 6 is released whereby its corresponding spring member 29 (shown in FIG. 7) biases leading edge 11 into an aligned notch 14 of push rod 5. Because brace 8 of head member 7 is constantly biased against the forward end 13 of push rod 5 due to the force supplied by spring member 40 (shown in FIG. 8) as well as by the force of the retracted anatomy, blade 9 will remain in the desired position.

The adjustments shown in FIGS. 4(a) and 4(b) may all be accomplished after the cylindrical mounting arm 2 is secured to extension arm 54 via joint clamp 55. Indeed, rather than having to make the multi-step adjustments currently practiced in the prior art or having to replace blade 9 with one having a different angular shape, the above-described procedure allows the surgeon the most precise means of retractor blade positioning with the least amount of adjustment effort. At a minimum, even if it is desired to change the position of cylindrical mounting arm 2 with respect to extension arm 54, the unique angling feature of the preferred embodiment alleviates the necessity of having to change blades 9 when a different blade angle is needed.

Figure 5A:
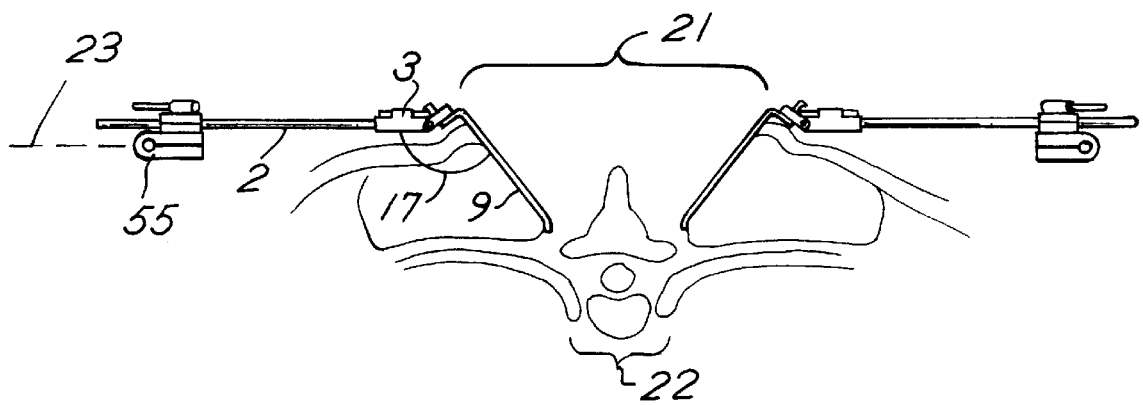
FIGS. 5(a), 5(b) and 5(c) are side views of the angling surgical retractor apparatus being used in three different angular positions.
Figure 5B:
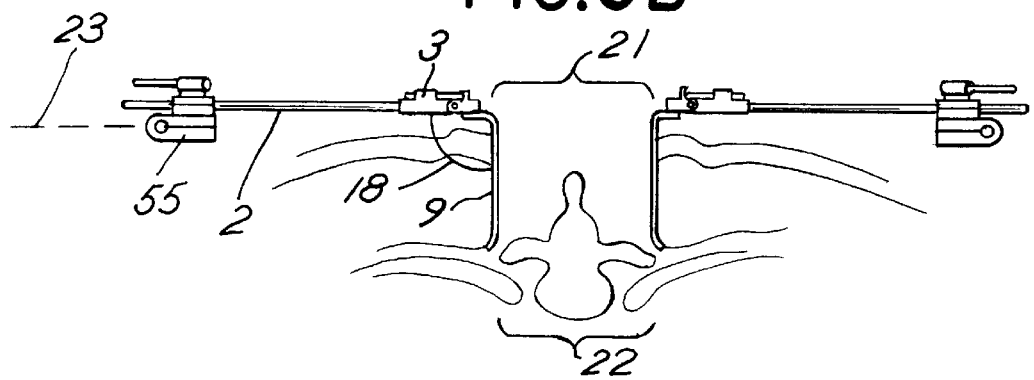
Figure 5C:
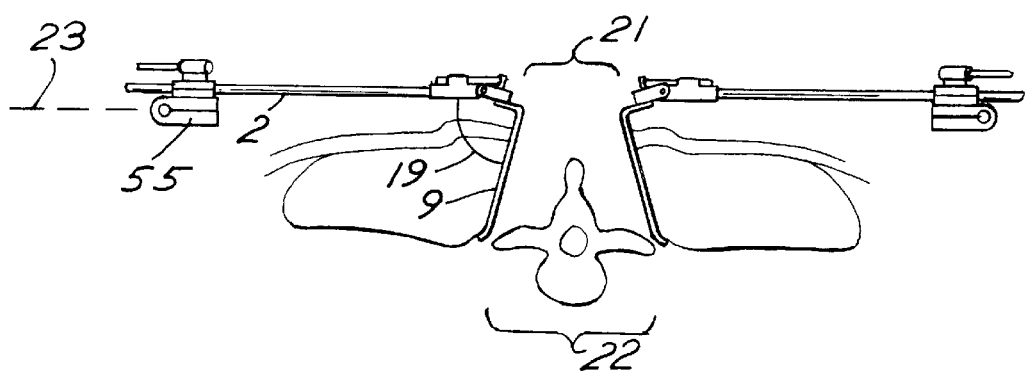

FIGS. 5(a), 5(b) and 5(c) represent side views of the preferred embodiment in actual use whereby the desirability of the unique angling feature may be more particularly observed. FIG. 5(a) shows the blade 9 at an obtuse angle 17 with respect to its associated body segment 3 and cylindrical mounting arm 2. Cylindrical mounting arm 2 is, in turn, secured in place to an extension arm (not shown) via joint clamp 55. Such configuration affords the greatest surgical opening 21 and smallest lower operating area 22.

FIG. 5(b) shows an adjustment of the retractor assembly whereby the blade 9 has been repositioned so as to be at a 90° angle 18 with respect to body segment 3. Here, the surgical opening 21 is approximately equal to the lower operating area 22. Such retractor blade adjustments could, if so desired, be made without ever having to adjust joint clamp 55 or the overall position of cylindrical mounting arm 2. Indeed, the horizontal mounting level 23 of these components is the same as that horizontal mounting level 23 as shown in FIG. 5(a)

As a further example, the retractor apparatus may be further adjusted to provide a relatively acute angle 19 between the blade 9 and body segment 3. Such may be the desired configuration when maximum exposure of the lower operating area 22 is required through a relatively narrow surgical opening 21. Again, joint clamp 55 and cylindrical mounting arm 2 may remain at horizontal mounting level 23 as no adjustments are necessary to these elements.

Referring now to FIG. 6, cylindrical mounting arm 2 is formed at its distal end to include a body segment 3 and is intended to be affixed at its proximate end to a standard joint clamp. The proximate end of cylindrical mounting arm 2 is cylindrical in shape having dimensions typical of other devices known in the art allowing for easy integration into existing retraction systems.

Body segment 3 is rectangularly-shaped in the preferred embodiment, but may take on other shapes including cylindrical, for example, thus being merely an extension of the shape of the cylindrical mounting arm 2. Body segment 3 provides a pivotal mounting for head member 7. If the embodiment includes a mechanism for securing or fixing the blade 9 to a pivotal position, the body segment 3 may be used to locate and support the fixing mechanism. The embodiment shown includes a fixing mechanism formed of a push rod housing 4, push rod 5, thumb switch 6 and spring 29 (shown in FIG. 7). Push rod housing 4 is integrally formed to, and positioned on top of, body segment 3 so as to be well outside that area of the device which contacts the retracted anatomy.

Push rod housing 4 has a substantially square-shaped bore through which push rod 5 is slidably received. Push rod 5 may freely move forward and backward within the bore of push rod housing 4 limited only by stop screws 15. Stop screws 15 are provided at the ends of, and top of, push rod 5 and extend upwardly a sufficient distance to inhibit the push rod's further movement by stop screws 15 engaging push rod housing 4.

Thumb switch 6 is arcuate in overall shape and pivotally mounted to push rod housing 4 via screw 28. Thumb switch 6 carries leading edge 11 adjacent to notches 14. Leading edge 11 and notches 14 are shaped so that leading edge 11 may be slid into any one of notches 14 to prevent sliding movement of push rod 5. A spring member 29 is looped about screw 28 having one end contacting push rod housing 4 and the other end biased against thumb switch 6. A force exerted by spring member 29 serves to bias the leading edge 11 of thumb switch 6 into one of the notches 14.

At the forward-most end of body segment 3 is mounted a cylindrical axle 10. Head member 7 is pivotally mounted to body segment 3 by a pair of pivot arms 36 which are secured to axle 10. Head member 7 includes a brace 8 which is positioned for being constantly biased against forward end 13 of push rod 5 via a spring member 40 (shown in FIG. 8) mounted to axle 10. Head member 7 also includes a nipple receptacle 33 disposed on the underside of head member 7 and into which a nipple 31 of blade 9 may be detachably received. Nipple 31 of an associated blade 9 is held within the nipple receptacle 33 by a spring-and-ball structure 46 to allow for releasable detachment of the blade 9 to the head member 7.

As will suggest itself, blade 9 and head member 7 may be integrally-formed together as a single blade member. The use of two members as shown herein allows for the detachability and use of a variety of blades 9 with a single head member 7.

Blade 9 may be angularly adjusted with respect to body segment 3 so as to be retained at one of any number of angular positions, shown generally at 25. Shown in FIG. 6 are examples of a partially retracted angular position 26 and a partially extended angular position 27 of the blade 9.

FIG. 7 offers a top view detail with the blade 9 substantially at a 90° angle with respect to body segment 3. Spring member 29 is biased between rod housing 4 and thumb switch 6 whereby the outward force of spring member 29 against the outer end of thumb switch 6 serves to rotate the leading edge 11 into one of several notches 14 formed on the side of push rod 5. As shown in more detail, pivot arms 36 of head member 7 are placed over the axle 10 immediately adjacent the sides of body segment 3.

Head member 7 is shaped to include a projection 34 through which is formed a channel 35 to receive a spring-and-ball structure. Channel 35 traverses the length of projection 34 to allow the spring-and-ball structure 46 to be inserted into the end of channel 35 to engage a nipple 31 of associated blade 9. Pursuant to the preferred embodiment, and as known in the prior art, nipple 31 of blade 9 is detachably received within nipple receptacle 33 of head member 7. Blade 9 is then allowed to swivel about swivel point 32 in a direction indicated generally at 30.

Turning now to FIG. 8, a close-up top view of the present device is offered whereby the angling feature may be more particularly observed. The forward most end of body segment 3 is comprised of a pivot member 37 and notched corner 38. Traversing both of these sections, as well as the adjoining pivot arms 36 of head member 7, is the device's axle 10. Positioned around axle 10 within the notched corner 38 is the spring member 40 which provides the biasing force between brace 8 of head member 7 and the forward end 13 of push rod 5. Specifically, a first end of spring member 40 remains in contacting relation with rearward face 43 of notched corner 38 while a second end of spring member 40 remains in contacting relation with a rearward face 44 of head member 7. Such an arrangement assures that the head member 7 and associated blade 9 remains in the desired angular position while not having to physically connect the head member 7 to the push rod 5. In accordance with the preferred operation of the present device, the retracted anatomy which is positioned on the backside of blade 9 also serves to place a biasing force on the blade 9 whereby brace 8 of head member 7 is further pushed into contacting relation with the forward end 13 of push rod 5.

FIG. 9 is a side view of the preferred embodiment, opposite that which is shown in FIG. 6. Here it may be observed that the substantial underside of the device is free from the variety of adjustment components which are incorporated into this device's design. Such design ensures that this underside area remain unobstructed during a retraction procedure. Again, forward end 13 of push rod 5 remains in engagement with brace 8 of head member 7 at all times during angular repositioning of the blade 9 about axle 10.

Lastly, FIG. 10 shows the detachability feature of the present device whereby the nipple 31 of blade 9 is detachably received, and secured, within nipple receptacle 33 of head member 7 such that the upper surface 45 of blade 9 is positioned adjacent the lower surface of head member 7. Commonly known within this field of art, this arrangement allows the blade 9 to swivel in place to the desired swivel position. Thus, in addition to the unique angling feature proposed, the angling surgical retractor apparatus still provides the flexibility to use variously-shaped retractor blades which are available on the market.

While the present invention has been illustrated in some detail according to the preferred embodiment shown in the foregoing drawing and description, it would be apparent to those skilled in the relevant art that variations and equivalents may be made thereto without departing from the spirit and scope of the invention as set forth in the appended claims. Indeed, the particular notched push rod assembly is not critical to the design of the present invention as such adjustments could be provided via screw threads, rotary shaft assembly, etc. Similarly, the engagement of such mechanism could be accomplished by any number of mechanical elements which could inhibit the movement of the push rod. In addition, the biasing feature of the present invention which keeps the brace 8 in contacting relation with push rod 5 might be accomplished by exerting a force on the push rod 5, rather than the head member 7. As it is the angular adjustability of the blade 9 which is so new to this field of art, the variety of inconsequential means of providing such angular movement and thereafter securing the blade should all be considered within the contemplation of the present invention.

We claim:

1. An apparatus for use by an operator for retracting anatomy at a surgical site during surgery, the apparatus comprising:
   a handle rod having a shape for securement relative to a surgical site;
   a retractor blade member pivotally mounted to a distal end of said handle rod and pivotal to a plurality of discrete angular positions relative to said rod;
   a securing mechanism fixedly mounted to said handle rod and contacting said retractor blade member adjacent said distal end of said handle rod, said securing mechanism being actuable by the operator, said retractor blade fixable by the operator in one of said discrete angular positions by actuation of said securing mechanism.

2. The apparatus of claim 1, wherein said securing mechanism includes a push rod slidably mounted to said handle rod and positionable at a plurality of rod positions relative to said handle rod for contact with said retractor blade member, said push rod establishing a different angular position of said retractor blade at each of said rod positions.

3. The apparatus of claim 2, wherein said securing mechanism further comprises a latch secured to said handle rod, said latch being engageable with said push rod at a plurality of different rod locations.

4. The apparatus of claim 3, wherein said push rod includes a plurality of notches for engagement with said latch.

5. The apparatus of claim 3, wherein said latch includes a biasing member for biasing said latch into engagement with one of said notches.

6. The apparatus of claim 2, further comprising a biasing member contacting said retractor blade and said securing mechanism, said biasing member for forcing said retractor blade member and said push rod into contact.

7. The apparatus of claim 6, wherein said biasing member is a spring.

8. The apparatus of claim 2, wherein said securing mechanism includes a push rod housing having a bore for slidably receiving said push rod.

9. The apparatus of claim 2, wherein said push rod includes a plurality of stops, each one of said stops corresponding to one of said plurality of rod positions.

10. The apparatus of claim 1, wherein said retractor blade member includes a blade portion and a head member portion, said head member portion being pivotally mounted to said handle rod.

11. The apparatus of claim 10, wherein said blade portion and said head member portion are discrete components connected together.

12. The apparatus of claim 11, wherein said blade portion is detachably mounted to said head member portion.

13. The apparatus of claim 10, wherein said head member portion includes a contact area for receiving contact with said push rod.

14. A method of retracting anatomy during surgery, the method of comprising the steps of:
   providing a surgical retractor apparatus having a handle rod, a retractor blade, and a securing mechanism, said handle rod including a proximate end and a distal end, said retractor blade being pivotally connected to said distal end and pivotal to a plurality of angular positions, said securing mechanism fixedly mounted to said handle rod and contacting said retractor blade member adjacent said distal end of said handle rod;
   attaching said proximate end of said handle rod to a support rod connected to a surgical operating table;
   pivoting said retractor blade with respect to said handle rod to achieve a desired angle between said retractor blade and said handle rod for retracting said anatomy during surgery; and
   actuating said securing mechanism to secure said retractor blade at said desired angle.

15. The method of claim 14, wherein said step of actuating said securing mechanism further includes the steps of:

providing said securing mechanism with a push rod slidably mounted upon said handle rod;

moving said push rod into engagement with said retractor blade;

engaging a latch mounted upon said handle rod with said push rod to subsequently inhibit further movement of said push rod; and biasing said push rod into engagement with said retractor blade.

16. The method of claim 15, further comprising the steps of:

providing said retractor blade with swivel capability with respect to said handle rod; and swiveling said retractor blade with respect to said handle rod to achieve a desired swivel position.

17. A method of retracting anatomy during surgery, the method comprising the steps of:

providing a surgical retractor apparatus having a handle rod, a head member, a retractor blade, and a securing mechanism, said handle rod including a proximate end and a distal end, said head member being pivotally connected to said distal end and pivotal to a plurality of angular positions, said retractor blade releasably engageable with said head member for conjoint movement therewith said securing mechanism fixedly mounted to said handle rod and contacting said head member adjacent said distal end of said handle rod;

attaching said proximate end of said handle rod to a support rod connected to a rail of a surgical operating table;

pivoting said head member and retractor blade with respect to said handle rod to achieve a desired angle between said retractor blade and said handle rod for retracting said anatomy during surgery; and actuating said securing mechanism to secure said head member at said desired angle.

18. The method of claim 17, wherein said step of actuating said securing mechanism further includes the steps of:

providing said securing mechanism with a push rod slidably mounted upon said handle rod;

moving said push rod into engagement with said head member;

engaging a latch mounted upon said handle rod with said push rod to subsequently inhibit further movement of said push rod; and biasing said push rod into engagement with said head member.

19. The method of claim 18, further comprising the steps of:

providing said retractor blade with swivel capability with respect to said head member; and swiveling said retractor blade with respect to said head member to achieve a desired swivel position.

* * * * *